(12) United States Patent
Krumme et al.

(10) Patent No.: US 8,594,480 B2
(45) Date of Patent: Nov. 26, 2013

(54) ROTATING DATA TRANSMISSION DEVICE

(75) Inventors: Nils Krumme, Feldafing (DE); Georg Lohr, Eichenau (DE)

(73) Assignee: Schleifring und Apparatebau GmbH, Fuerstenfeldbruck (DE)

( * ) Notice: Subject to any disclaimer, the term of this patent is extended or adjusted under 35 U.S.C. 154(b) by 2009 days.

(21) Appl. No.: 11/536,237

(22) Filed: Sep. 28, 2006

(65) Prior Publication Data

US 2007/0063785 A1  Mar. 22, 2007

Related U.S. Application Data

(63) Continuation of application No. PCT/EP2005/003396, filed on Mar. 31, 2005.

(30) Foreign Application Priority Data

Mar. 31, 2004 (DE) .................... 10 2004 016 525
Jun. 28, 2004 (DE) .................... 10 2004 031 355

(51) Int. Cl.
*G02B 6/00* (2006.01)
*H01P 5/12* (2006.01)
*A61B 6/00* (2006.01)
*G06K 9/00* (2006.01)

(52) U.S. Cl.
USPC .............. 385/147; 378/4; 378/15; 378/19; 378/98.8; 382/131; 333/24 R; 333/113

(58) Field of Classification Search
USPC ........... 378/4, 901, 98.8, 15, 19; 385/15, 31, 385/147; 340/500; 333/24, 113; 382/131
See application file for complete search history.

(56) References Cited

U.S. PATENT DOCUMENTS

| | | | | |
|---|---|---|---|---|
| 4,644,573 | A * | 2/1987 | Palermo et al. | 378/15 |
| 4,692,721 | A * | 9/1987 | Ito et al. | 333/109 |
| 5,530,422 | A * | 6/1996 | Harrison | 340/500 |
| 5,530,423 | A * | 6/1996 | Harrison | 340/500 |
| 5,600,697 | A * | 2/1997 | Harrison | 378/15 |
| 6,144,267 | A * | 11/2000 | Saitoh et al. | 333/34 |
| 6,181,766 | B1 * | 1/2001 | Pearson et al. | 378/15 |
| 6,301,324 | B1 * | 10/2001 | Pearson et al. | 378/15 |
| 6,580,853 | B2 * | 6/2003 | Harrison et al. | 385/31 |
| 2002/0111047 | A1 * | 8/2002 | Jacobson | 439/19 |

OTHER PUBLICATIONS

Ibanescu et al., "An All-Dielectric Coaxial Waveguide", Jul. 2000, Science, vol. 289, No. 5478, pp. 415-419.*
International Search Report, PCT/EP2005/003396, mailed Jul. 12, 2005.
Meinke et al. "Taschenbuch der Hochfrequenztechnik S.," pp. 308-313, © 1968 Springer-Verlag.

* cited by examiner

*Primary Examiner* — Mark Robinson
*Assistant Examiner* — Guy Anderson
(74) *Attorney, Agent, or Firm* — Kevin L. Daffer; Daffer McDaniel LLP

(57) ABSTRACT

A rotating data transmission device for computer tomographs, for transmission from a rotating part to a stationary part that is rotatably supported relative to the rotating part, comprises at least one dielectric waveguide assigned to the rotating part, at least one first line coupler for coupling electrical signals into the at least one dielectric waveguide, and at least one coupler assigned to the stationary part for tapping electrical signals from the at least one dielectric waveguide. The dielectric waveguide is divided into at least two segments of approximately the same length, signals are coupled into the segments of the dielectric waveguides through a first line coupler to propagate in opposite directions, and ends of the segments distant from the line coupler are provided with terminations.

24 Claims, 8 Drawing Sheets

ROTATING DATA TRANSMISSION DEVICE

CONTINUING DATA

This application is a continuation of pending International Application No. PCT/EP2005/003396 filed Mar. 31, 2005, which designates the United States and claims priority from pending German Applications Nos. 102004016525.4 filed Mar. 31, 2004 and 102004031355.5 filed Jun. 28, 2004.

BACKGROUND OF THE INVENTION

1. Field of the Invention

The invention relates to a rotating data transmission device, in particular for use in computer tomographs. Here a transmission of digital image data obtained by an X-ray detector is effected in a non-contacting manner between a rotatable gantry and a stationary part of a computer tomograph. Furthermore, data can also be transmitted in the opposite direction to control the rotatable gantry.

2. Description of the Prior Art

A device for non-contacting rotating data transmission in computer tomographs is known from U.S. Pat. No. 5,530,422. In this, a signal to be transmitted is fed into a differentially operated strip conductor line on a rotating gantry, and is tapped off by a capacitive probe on the stationary part. Devices of this kind are usable up to data rates of an order of magnitude of approximately 1 Gbaud. This limit may be shifted slightly to higher values by further developments, as disclosed for example in U.S. Pat. No. 6,181,766. For this, suitable encodings or modulation methods are employed.

BRIEF SUMMARY OF THE INVENTION

The invention is based on the object of improving prior art devices for non-contacting transmission of digital signals between two units that are movable relative to each other, and in particular between a stationary and a rotating part of a computer tomograph, so that wider-band signal transmission becomes possible with less stray radiation, a higher resistance to interference, and a lower bit error rate.

In accordance with the invention, this object is achieved by a rotating data transmission device for computer tomographs, for transmission from a rotating part that includes a transmitter for generating electrical signals to a stationary part that is rotatably supported relative to the rotating part and includes a receiver for receiving electrical signals; comprising: at least one dielectric waveguide assigned to the rotating part; at least one first line coupler for coupling electrical signals from the transmitter into the at least one dielectric waveguide; and at least one coupler assigned to the stationary part for tapping electrical signals from the at least one dielectric waveguide and relaying the tapped electrical signals to the receiver; wherein the dielectric waveguide is divided into at least two segments of approximately the same length; wherein signals are coupled into the segments of the dielectric waveguides through a first line coupler to propagate in opposite directions; and wherein ends of the segments distant from the line coupler are provided with terminations.

BRIEF DESCRIPTION OF THE DRAWINGS

In the following, the invention is described by way of example without limitation of the general inventive concept on examples of embodiment and with reference to the drawings.

DETAILED DESCRIPTION OF THE INVENTION

Figure 1:
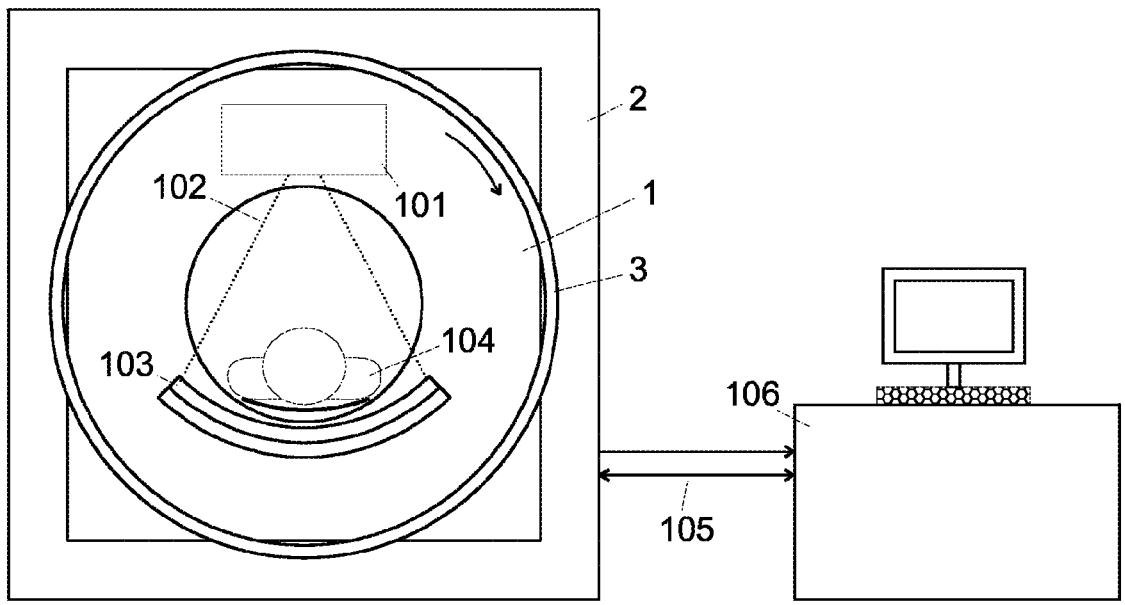
FIG. 1 shows by way of example a computer tomograph comprising a device in accordance with the invention.

FIG. 1 shows by way of example a device in accordance with the invention. The computer tomograph (CT scanner) consists of two main mechanical components. A stationary part 2 serves as a basis and a support for the entire instrument, in which the rotating part 1 rotates. A patient 104 is positioned on a berth inside the opening of the rotating part. An X-ray tube 101 and a detector 103 disposed opposite thereto are provided for scanning the patient by means of X-rays 102. The X-ray tube 101 and the detector 103 are rotatably disposed on the rotating part 1. A rotating data transmission device 3 serves as an electrical connection between the rotating part 1 and the stationary part 2. With this, high electrical power for feeding the X-ray tube 101 is transmitted in a direction towards the rotating part 1, and at the same time video data are transmitted in the opposite direction. A communication of control information in both directions is provided in parallel with this. An evaluation and control unit 106 serves for operating the computer tomograph, and also for displaying generated images. Communication with the computer tomograph is effected via a bidirectional link 105.

Figure 2:
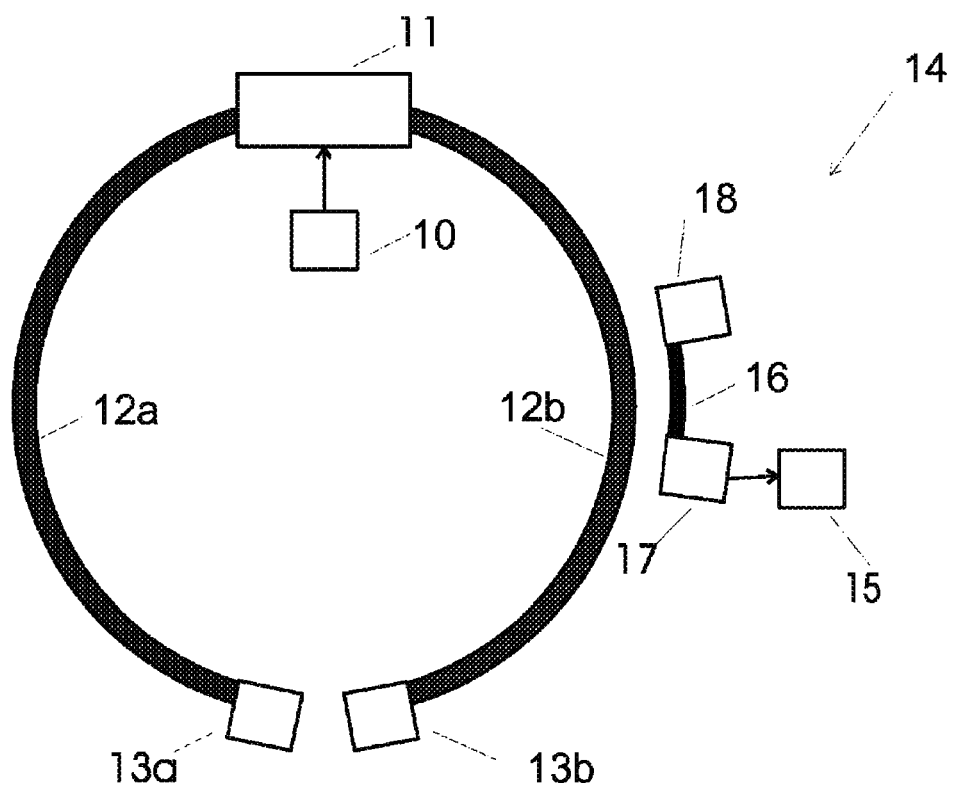
FIG. 2 shows schematically a device in accordance with the invention.

FIG. 2 shows by way of example a device according to the invention in detail. A transmitter 10, for example an X-ray detector of a computer tomograph on its rotating gantry, serves to emit high-frequency signals into a first line coupler 11, and from there into a dielectric waveguide 12a, 12b that is divided into two. This first line coupler may be constructed optionally according to dielectric waveguide technology, or also pure electrical technology. Branches of the divided dielectric waveguide are terminated at their ends by means of terminations 13a, 13b to be substantially free from reflections. Disposed to be relatively movable thereto, or on the stationary part of the gantry, is a receiver 15 for receiving the signals tapped from the coupler 14. The coupler 14 is preferably also provided with a dielectric waveguide 16, and preferably couples out the field in the vicinity of the first dielectric waveguide 12a, 12b on the transmitter side without contact. This may be effected, for example, by a coupling of evanescent fields through a second line coupler 17. For this, the dielectric waveguide 16 is preferably designed as a dielectric of the same kind as the dielectric waveguide 12a, 12b, and furthermore, both are guided with respect to each other with as small as possible a gap preferably <lambda/6), either without contact, or by utilizing sliding properties. This dielectric waveguide 16 is preferably also closed off to be free from reflection by means of a termination 18. The first line coupler 11 need not be disposed, as is shown here, in close proximity to the dielectric waveguide 12a, 12b. Rather than this, it also may be disposed at a distance and, for example, incorporated in the transmitter 10. The signal connection between the first line coupler 11 and the dielectric waveguide 12a, 12b is effected preferably via extended ends of the dielectric waveguide 12a, 12b, or by interposed additional dielectric waveguides. The same applies in an analogous manner to the second line coupler 17 and the dielectric waveguide 16.

Figure 3:
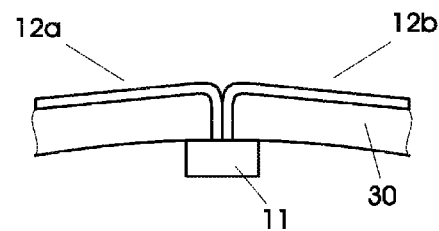
FIG. 3 shows the coupling-on of a line coupler to a dielectric waveguide.

FIG. 3 illustrates by way of example an arrangement with a dielectric waveguide 12a, 12b that is divided into two, and a first line coupler 11 on a mechanical support 30 of the rotating data transmission device. In this example the parts of the dielectric waveguide are guided on the outside by the support 30 for scanning by the coupler 14. An embodiment in which the dielectric waveguide is scanned on the inside of the support would have to be designed appropriately conversely.

Figure 4:
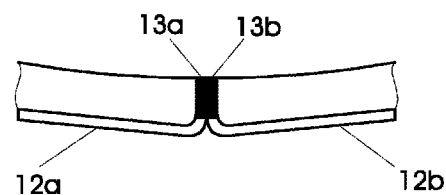
FIG. 4 shows the termination of a dielectric waveguide.

FIG. 4 illustrates by way of example a termination 13a, 13b of the dielectric waveguide 12a, 12b. Here a termination can be effected by jointly closing off both parts of the dielectric waveguide, or by separate terminations.

Figure 5:
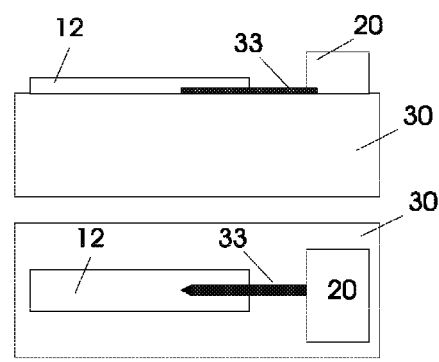
FIG. 5 shows an electrical coupling-on to a dielectric waveguide.

FIG. 5 shows an example of an electric coupling of an electrical transmitter 20 onto the dielectric waveguide 12 by means of a strip line 33. The arrangement is located on an electrically insulating support 30. The strip line projects into the end of, or is located below, the dielectric waveguide and is designed so that a transmission of electrical signals is effected that is as free as possible from reflections.

Figure 6:
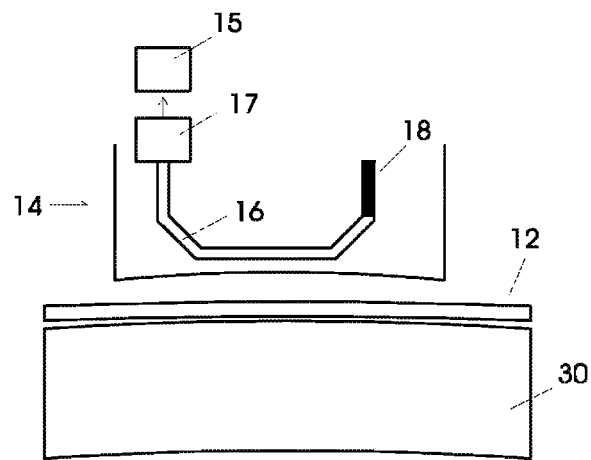
FIG. 6 shows the construction of a coupler.

FIG. 6 shows a side view of a coupler 14 that is guided along a dielectric waveguide 12. The coupler comprises a dielectric waveguide 16 for tapping a part of the signal of the dielectric waveguide 12 and passing it on to a receiver 15 by means of a second line coupler 17. The other end of the dielectric waveguide 16 is closed off in a manner free from reflection by the termination 18.

Figure 7:
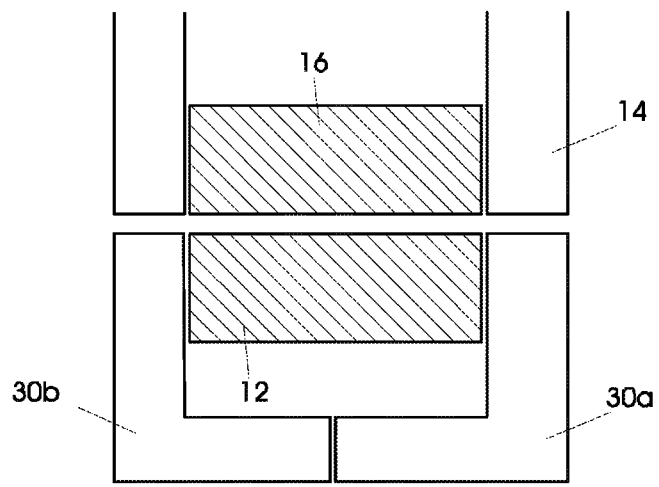
FIG. 7 shows a cross-section of device in accordance with the invention.

FIG. 7 illustrates a section of a device in accordance with the invention. A dielectric waveguide 12 is guided, by way of example, in a support 30a, 30b that is divided into two and is preferably made of an electrically conducting material. For tapping signals from the dielectric waveguide 12, a coupler 14 is provided that also comprises a dielectric waveguide 16.

Figure 8:
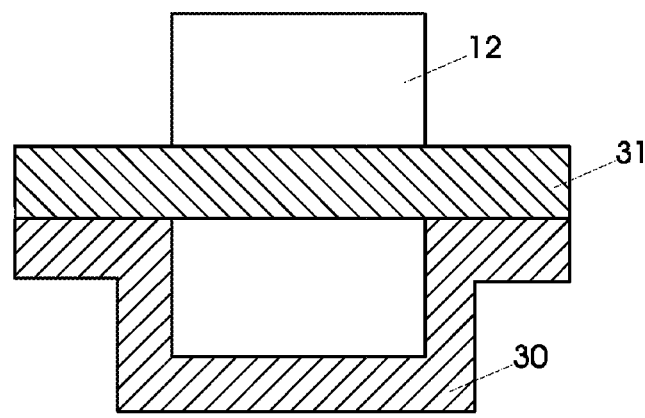
FIG. 8 shows by way of example an alternative construction of a dielectric waveguide.

FIG. 8 illustrates yet another embodiment of a dielectric waveguide. An electrically conducting, preferably metallic support 30 having a recess is covered by a support plate 31 made of a dielectric. Now the dielectric waveguide 12 is mounted on this.

Figure 9:
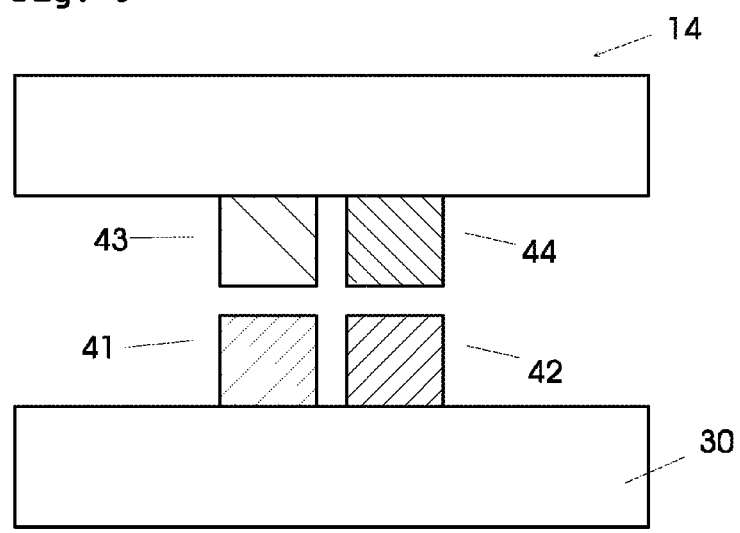
FIG. 9 shows by way of example an alternative construction of a dielectric waveguide.

FIG. 9 shows a differential embodiment of the invention, in which the first dielectric waveguide 12 consists of two part-waveguides 41 and 42. The two part-waveguides are fed with differential signals. This means, for example, that the sum of the signal amplitudes of the part-waveguides 41 and 42 at the interface of the drawing is zero at any instant of time. Accordingly and in an advantageous manner, the coupler 14 is also constructed to be differential, having the two part-waveguides 43 and 44.

Figure 10:
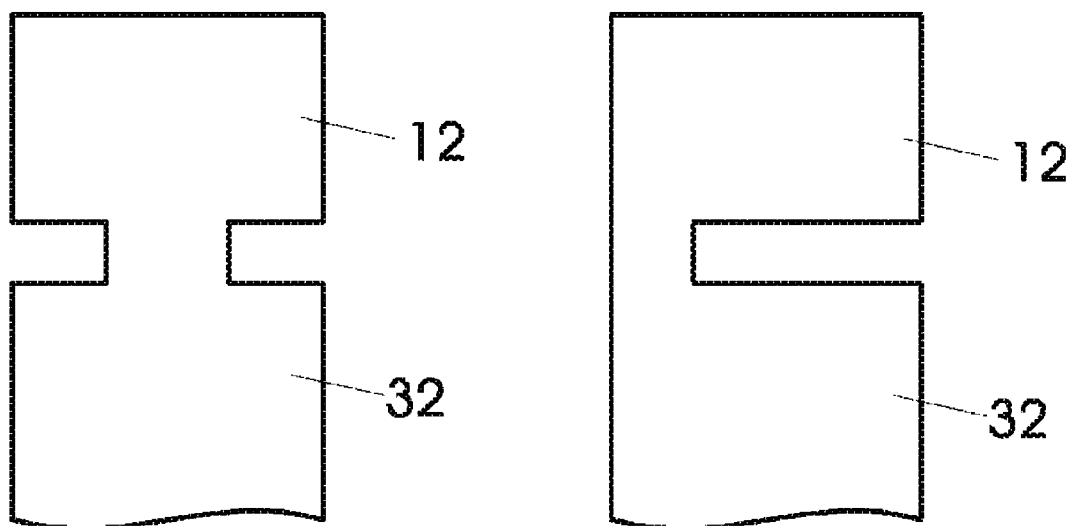
FIG. 10 shows an incorporation of a dielectric waveguide into a slipring.

FIG. 10 illustrates the incorporation of a dielectric waveguide into a slipring. A mechanical slipring body 32 (slipring module) supports the dielectric waveguide 12, for example on the outside. Of course, the dielectric waveguide may also be disposed on the inside or on the face. It is particularly advantageous for the slipring body and the dielectric waveguide to be made of the same material. A connecting web for holding the dielectric waveguide to the slipring body may be manufactured as a separate component, but most preferably by machining the slipring body. In this example, the connecting web has been made by turning (recessing). The configuration of the connecting web is governed by the modes of the electromagnetic wave to be transmitted.

Figure 11:
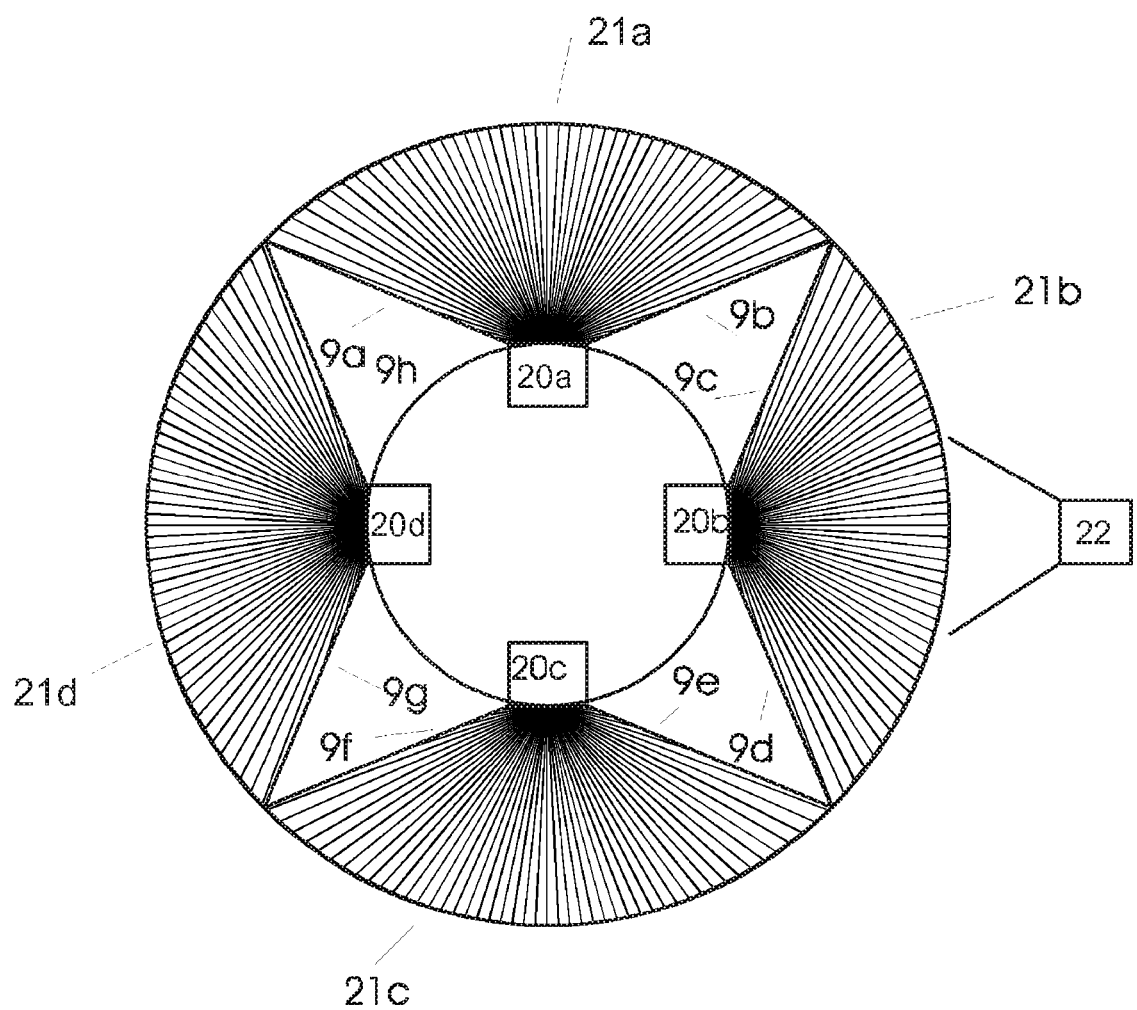
FIG. 11 shows another embodiment of the invention comprising a plurality of transmitters.

FIG. 11 illustrates another embodiment of the invention. In this, the dielectric waveguide 12 is divided into a plurality of sections 21a, 21b, 21c, 21d. This is effected by the separating faces 9a-9h. These separating faces may be embodied optionally by metallized layers, or also by a transition to a different dielectric having a different dielectric constant. They serve for guiding or focusing the signals from the individual transmitters 20a, 20b, 20c, 20d. These signals are now carried in the dielectric enclosed between the separating faces. The receiver 22 is adapted to be movable relative to this arrangement and may be designed, for example, like a horn antenna with or without a dielectric. It may have a configuration similar to that on the transmitter side, and include a dielectric and the separating faces.

Figure 12:
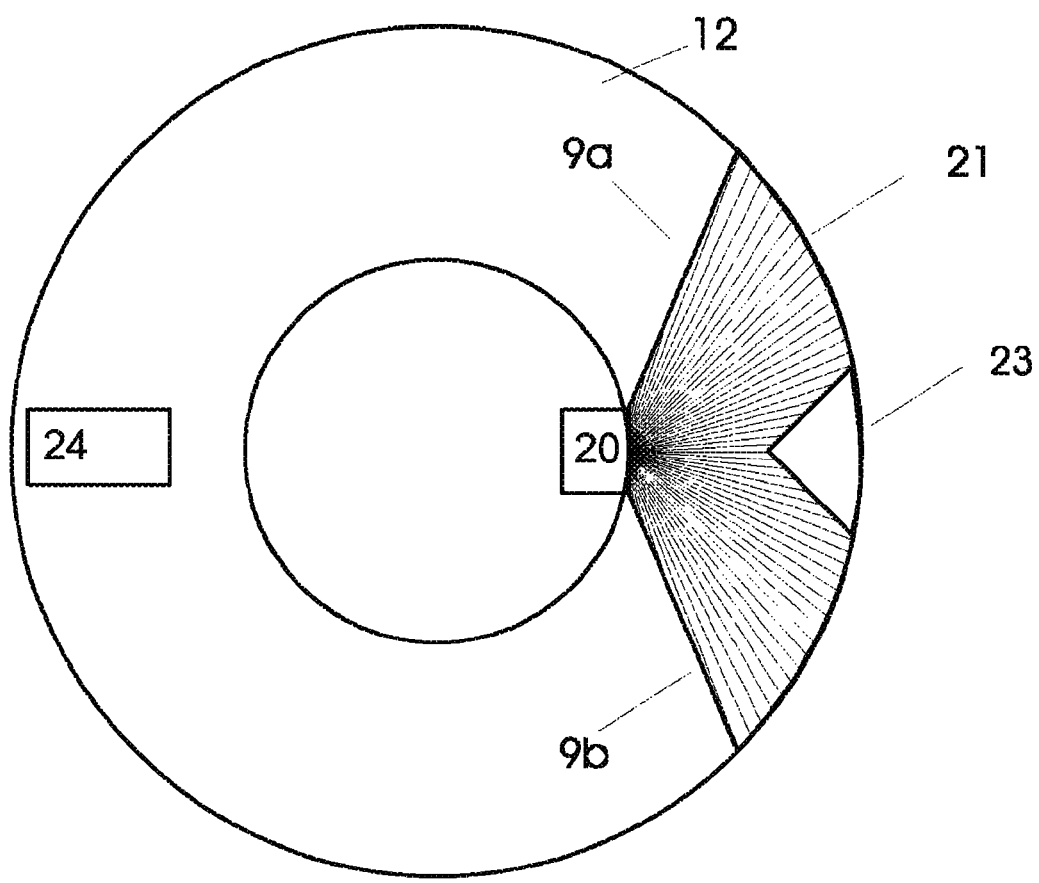
FIG. 12 shows another embodiment of the invention comprising a single transmitter.

FIG. 12 shows another embodiment of the invention in which the coupling-in of the high-frequency energy of the transmitter 20 into an annular dielectric waveguide 12 is effected by means of a reflector 23. The separating faces 9a, 9b may be utilized for controlling the field. However, the device is capable of operation without these separating faces. Basically, the entire inner space between the two circular boundaries may be filled with a dielectric. The high-frequency energy emitted by the transmitter may now spread out in the form of a circle in this dielectric. An absorber 24 prevents multiple circulation of the electromagnetic wave.

To simplify the explanations, repeated reference will be made in the following to a transmission from the rotating part to the stationary part of a computer tomograph. Of course, a device in accordance with the invention may also be used in the opposite direction of transmission. Similarly, a device in accordance with the invention may also be utilized in other applications of rotary transmission, and similarly for linear transmission between two units that are movable relative to each other.

The invention comprises a device for non-contacting transmission of electrical and, in particular, digital signals. Transmission is effected by means of dielectric waveguides which are preferably designed to be NRD (Non Radiating Dielectric). Thus, a transmitter 10 on a rotating part (rotor) generates electrical signals which are coupled into a dielectric waveguide 12a, 12b via a first line coupler 11. The signals are carried in the dielectric waveguide and absorbed at its end by a termination 13a, 13b. For coupling out the signals carried in the dielectric waveguide, at least one coupler 14 is provided on the stationary part. This coupler 14 is moved in the vicinity of the dielectric waveguide 12a, 12b. It couples out a part of the electrical energy of the signals of the dielectric waveguide and transmits this to a receiver 15 on the stationary part (stator). By way of example, the dielectric waveguide may be disposed in a known manner on a metallic substrate. For this, the arrangement is dimensioned so that an electromagnetic wave from the signal to be transmitted is propagated in the dielectric, preferably with only one single mode. As an alternative to this, the propagation may also be effected with a surface wave in the dielectric. This, in turn, may be excited within the dielectric itself. Coupling onto the dielectric waveguide is effected preferably with directional couplers, or an adjacent waveguide structure, or by means of a hollow-guide wave, or a conductor line which is preferably a strip line, or a micro-strip line which is particularly preferred, or also via prisms, or a grid structure of the waveguide.

In a particularly advantageous embodiment of the invention, the coupler 14 is an electric coupler for coupling signals from the dielectric waveguide so that they can be carried in a conductor line, for example as a TEM wave. For this, the coupler itself is preferably constructed according to strip-line technology.

In another advantageous embodiment of the invention, the coupler 14 itself comprises a dielectric waveguide 16. Now, connected to this dielectric waveguide is a second line coupler 17 for converting the signals carried in the dielectric waveguide 16 of the coupler 14 to electrical signals which may be carried in a conductor, for example as a TEM wave.

In another advantageous embodiment of the invention the second line coupler 17 is attached to one end of the dielectric waveguide 16. At the same time, a termination 18 for terminating the dielectric waveguide 16 in a manner free from reflection is provided at the other end of the dielectric waveguide 16.

Another advantageous embodiment of the invention provides for at least one of the terminations 13a, 13b or 18 to be adapted as a termination in the form of a dielectric waveguide.

In another embodiment of the invention, at least one of the terminations 13a, 13b or 18 is designed to be a conductor coupler for conversions to a line wave, for example a TEM wave. Furthermore, an electrical absorber or terminal resistor is provided for termination, i.e. for terminating the electrical wave in a manner free from reflection, and connected to the line coupler.

Another advantageous embodiment of the invention comprises the design of the dielectric waveguide 12a, 12b as a differential conductor system. In this, two dielectric waveguides 41, 42 are disposed in parallel, and are supplied with a differential signal. Thus, the momentary value of a signal at a certain point of the first dielectric waveguide 41 is exactly inverse to the momentary value of the signal at the corresponding point of the second dielectric waveguide 42. Thus, the sum of the signals at each site on the dielectric waveguides 41 and 42 results in the value 0. This leads to a substantial reduction of electromagnetic emission.

In another advantageous embodiment of the invention, the coupler 14 is designed to be a differential coupler. This means that in the coupler only differential signals are evaluated for receipt. Common mode signals which, for example, are coupled uniformly into the two dielectric waveguides 41 and 42, or also into the two waveguides 43 and 44 owing to an external fault, may thus be suppressed or attenuated. Thus, interference signals of this kind no longer affect a wanted signal.

Another advantageous embodiment of the invention provides a modulator in the transmitter 10 for matching the data to be transmitted to the dielectric waveguide. Accordingly, a demodulator for recovering the data is provided in the receiver 15. A modulator of this kind converts the spectral range of the data to be transmitted to another spectral range that is more suitable for transmission via the dielectric waveguide. Here the modulation may be effected by all known methods, for example by mixing with a carrier, or also by encoding, or by combining a plurality of methods. The demodulation is matched in accordance with this. Here it is particularly efficient to employ a suitable encoding of the signals, so that the bandwidth of a signal to be transmitted is within the transmittable bandwidth of the dielectric waveguide.

In another advantageous embodiment of the invention, the dielectric waveguide 12a, 12b is divided into at least two segments. With a division into a plurality of segments, for example, a plurality of data streams may be transmitted simultaneously. For this, different data streams are fed into different segments, and simultaneously a plurality of receivers are provided for receiving the different data streams. Furthermore, owing to the segmentation, the length of the individual dielectric waveguides may be kept shorter. This results in reduced losses within the dielectric waveguides, and also in an increased resistance to interference. It is of particular advantage when altogether two segments of the dielectric waveguide are provided, which are of the same length. Furthermore, in this embodiment a common site for signal coupling-in is provided, from which the signals propagate in opposite directions in the segments of the dielectric waveguides. Terminations, for example in the form of absorbers, are provided at the end of the dielectric waveguide. With this embodiment, signals having the same phase are applied to the points of mutual approach of the two segments, that is, to the site of signal coupling-in and also to the site of the terminations.

In another embodiment of the invention, the dielectric waveguide 12 is divided into a multitude of short conductor segments. With this, in an advantageous manner, the length of the conductor segments is chosen to be so short that the reflections in the individual segments do not yet lead to a substantial impairment of the signals to be transmitted. Thus, a termination of the individual segments may be dispensed with. Particularly with rotating data transmission devices having small diameters of the order of a few centimeters, the dielectric waveguide 12 may be employed without termination. Optionally and similarly, it may be designed to be a closed ring.

Another advantageous embodiment of the invention provides for at least one of the terminations 13a, 13b or 18 to be designed in the form of absorbers in accordance with dielectric waveguide technology.

Another alternative of the invention provides for at least one of the terminations 13a, 13b or 18 to be designed as electrical terminal resistors, the coupling-on being effected via a dielectric conductor coupler.

Another advantageous embodiment of the invention provides for the coupler 14 to be designed as a directional coupler. Owing to its design as a directional coupler, it taps from the dielectric waveguide 12a, 12b only signals that propagate in a given direction. Thus, for example, interference signals propagating in an opposite direction may be suppressed. Furthermore, the use of directional couplers permits in a simple way and manner a transmission of a plurality of channels, or a bidirectional transmission. For unidirectional transmission of a plurality of channels, dielectric line couplers 11 should be disposed at different locations of the dielectric waveguides 12a, 12b, so that the different signals propagate along opposite directions of the same conductor branch.

Another advantageous embodiment of the invention comprises a bearing that is provided preferably in the vicinity of a coupler 14 to guide the coupler at a defined small distance from the dielectric waveguide 12. This bearing preferably comprises a hydrostatic or also hydrodynamic bearing, and an air bearing is especially preferred. Air bearings of this kind are characterized by being of simple design and highly robust, and particularly of high mechanical rigidity.

Furthermore, the subject matter of the invention is a rotating data transmission device (slipring) for transmission between units that are rotatable relative to each other, which comprises an above-described transmission path based on a dielectric waveguide. According to the invention, various advantageous embodiments of a dielectric waveguide may be incorporated in a slipring of this kind. Thus, for example, it may be integral with the material of the slipring itself. Also consisting of the same material, it could be joined to the inside or the outside of the slipring, being supported preferably at its middle, as seen along a radial direction, by a thin web. Similarly, the dielectric could also serve as a mechanical support for slide tracks for contacting electrical transmission. Furthermore, the dielectric waveguide itself could consist of two parts (preferably halves), with one part rotating and the other being stationary.

Other subject matter of the invention is a computer tomograph having at least one of the above rotating data transmission devices based on a dielectric waveguide for data transmission. For this, the transmission may, of course, be effected optionally from the rotating part to the stationary part or vice versa. Optionally a plurality of rotating data transmission devices may be employed for transmitting a plurality of signals, or for increasing the transmission rate.

Further subject matter of the invention is a method for transmitting data between units that are movable relative to each other, the signals of a transmitter being passed along a track of movement in a dielectric waveguide, and coupled out at a site of a receiver by means of a tap.

As an alternative to this, the signals may be transmitted in the dielectric waveguide within a limited range of a movement obliquely to the track of the movement.

A device in accordance with the invention may be embodied particularly simply and cheaply, because low cost dielectric materials such as polyethylene (PE) may be employed. Furthermore, standard radio modems may be employed for modulation. As a propagation of the electromagnetic field is limited to the dielectric of the dielectric waveguide, substantially less electromagnetic interference is emitted into the surroundings than, by way of comparison, in the case of technical solutions using radio transmission. At the same time, the system is, of course, less susceptible to interference, because it receives and evaluates only the signals carried in the dielectric waveguide. Owing to the electromagnetic signals being carried in a dielectric waveguide, a plurality of similar transmission means may be used in parallel and free from problems in a computer tomograph, without any conflict (cross-talk) arising. An "interception" of data to be transmitted is also not possible. Owing to the use of a dielectric waveguide, a substantially larger bandwidth is possible than with radio links, by way of comparison, because recourse may also be made to frequency bands that otherwise are not permitted. Because of the substantially better coupling through the dielectric waveguide, a substantially higher signal level, and therewith a better signal-to-noise ratio, results in the receiver.

The invention claimed is:

1. A rotating data transmission device for computer tomographs, for transmission from a rotating part that includes a transmitter for generating electrical signals to a stationary part that is rotatably supported relative to the rotating part and includes a receiver for receiving electrical signals, comprising:
    a first dielectric waveguide assigned to the rotating part for carrying electrical signals;
    a first line coupler for coupling electrical signals from the transmitter into the first dielectric waveguide;
    at least one coupler assigned to the stationary part for tapping electrical signals from the first dielectric waveguide and relaying the tapped electrical signals to the receiver;
    wherein the first dielectric waveguide is divided into at least two segments of approximately the same length;
    wherein signals coupled into the segments of the first dielectric waveguide through the first line coupler propagate in opposite directions; and
    wherein ends of the segments distant from the first line coupler are provided with terminations.

2. The device according to claim 1, wherein the at least one coupler comprises a second dielectric waveguide for coupling out signals from the first dielectric waveguide, and a second line coupler for converting the signals coupled into the second dielectric waveguide to electrical signals that are passed to the receiver.

3. The device according to claim 2, wherein the second line coupler converts signals of the second dielectric waveguide to electrical signals as a TEM wave.

4. The device according to claim 2, wherein at least one termination for terminating the second dielectric waveguide in a manner free from reflection is provided on the second dielectric waveguide.

5. The device according to claim 4, wherein at least one of the terminations is disposed at an end of the second dielectric waveguide opposite to the second line coupler.

6. The device according to claim 1, wherein at least one termination for terminating the first dielectric waveguide in a manner free from reflection is provided on the first dielectric waveguide.

7. The device according to claim 6, wherein the at least one of the terminations is disposed at an end of the first dielectric waveguide opposite to the first line coupler.

8. The device according to claim 4, wherein the at least one of the terminations is adapted to be a termination in the form of a dielectric waveguide attended by losses.

9. The device according to claim 6, wherein the at least one of the terminations is adapted to be a termination in the form of a dielectric waveguide attended by losses.

10. The device according to claim 4, wherein the at least one of the terminations comprises another line coupler for converting the signals carried in the second dielectric waveguide to a line wave, and this line coupler is connected to a termination free from reflection to absorb electrical energy.

11. The device according to claim 10, wherein the line wave is a TEM wave.

12. The device according to claim 6, wherein the at least one of the terminations comprises another line coupler for converting the signals carried in the first dielectric waveguide to a line wave, and this line coupler is connected to a termination free from reflection to absorb electrical energy.

13. The device according to claim 12, wherein the line wave is a TEM wave.

14. The device according to claim 1, wherein the first dielectric waveguide is designed to be a differential conductor system comprising two parallel dielectric waveguide segments to which a differential signal is applied.

15. The device according to claim 14, wherein the at least one coupler also comprises a differential coupling system.

16. The device according to claim 1, wherein a modulator for matching data to be transmitted to transmission characteristics of the first dielectric waveguide is assigned to the transmitter, and wherein a suitable demodulator for retrieving signals is assigned to the receiver.

17. The device according to claim 1, wherein the at least one coupler is designed to be a directional coupler, which receives signals carried in the first dielectric waveguide in a directionally selective manner.

18. The device according to claim 2, wherein the first line coupler or the second line coupler is designed to be a directional coupler.

19. The device according to claim 1, wherein a bearing is provided to guide the at least one coupler at a defined small distance from the first dielectric waveguide.

20. The device according to claim 19, wherein the bearing is a hydrostatic bearing or an air bearing.

21. The device according to claim 1, wherein the first dielectric waveguide is incorporated into a slipring body or a slipring module.

22. The device according to claim 21, wherein the first dielectric waveguide comprises the same material as the slipring body or slipring module.

23. A computer tomograph with a rotating part and a stationary part, comprising:
- at least one rotating data transmission device for transmitting signals from the rotating part to the stationary part or in an opposite direction, wherein the rotating data transmission device comprises:
- at least one dielectric waveguide for carrying electrical signals;
- at least one first line coupler for coupling electrical signals from a transmitter into the at least one dielectric waveguide;
- at least one coupler for tapping electrical signals from the at least one dielectric waveguide and relaying the tapped electrical signals to a receiver;
- wherein the dielectric waveguide is divided into at least two segments of approximately the same length;
- wherein signals are coupled into the segments of the dielectric waveguides through the first line coupler to propagate in opposite directions; and
- wherein ends of the segments distant from the first line coupler are provided with terminations.

24. A method for transmitting electrical signals between two parts that are rotatable relative to each other, in particular in a computer tomograph, comprising the following steps:
- feeding the signals from a transmitter into at least one dielectric waveguide;
- passing the electrical signals along a track of rotary movement, wherein the track comprises the dielectric waveguide; and
- coupling the electrical signals out of the at least one dielectric waveguide.

* * * * *